United States Patent
Chen et al.

(10) Patent No.: US 8,921,844 B2
(45) Date of Patent: Dec. 30, 2014

(54) OPTOELECTRONIC MATERIALS FOR OLED AND OLED ELEMENTS USING THE SAME

(71) Applicant: National Tsing Hua University, Hsinchu City (TW)

(72) Inventors: Chien-Tien Chen, Hsinchu (TW); Wei-Shan Chao, Hsinchu (TW); Hao-Wei Liu, Hsinchu (TW); Wei-Sheng Su, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 1 day.

(21) Appl. No.: 13/940,058

(22) Filed: Jul. 11, 2013

(65) Prior Publication Data

US 2014/0312311 A1   Oct. 23, 2014

(30) Foreign Application Priority Data

Apr. 17, 2013 (TW) .............................. 102113544 A (51) Int. Cl.
*H01L 51/00* (2006.01)
*H01L 35/24* (2006.01)

(52) U.S. Cl.
USPC .............. 257/40; 257/E51.001; 257/E51.041; 546/4; 428/690; 313/504

(58) Field of Classification Search
CPC ............ H01L 51/0085; H01L 51/0072; H01L 51/0074; H01L 51/0067; H01L 51/5012; H01L 51/0059; H01L 51/50; H01L 51/0035; H01L 51/0052; C09K 2211/185; C09K 2211/1037; C09K 2211/1433; H05B 33/14; H05B 33/20
USPC ................ 257/40, 85–95, 101–103, E51.001, 257/E51.041
See application file for complete search history.

(56) References Cited

U.S. PATENT DOCUMENTS

| | | | |
|---|---|---|---|
| 2007/0176174 A1* | 8/2007 | Lee et al. | 257/40 |
| 2009/0295278 A1 | 12/2009 | Lee et al. | |
| 2011/0253946 A1* | 10/2011 | Huh et al. | 252/501.1 |
| 2012/0326133 A1* | 12/2012 | Kim et al. | 257/40 |
| 2013/0113367 A1* | 5/2013 | Jung et al. | 313/504 |

* cited by examiner

*Primary Examiner* — Marcos D. Pizarro
*Assistant Examiner* — Nelson Garces
(74) *Attorney, Agent, or Firm* — Muncy, Geissler, Olds & Lowe, P.C.

(57) ABSTRACT

An optoelectronic materials for OLED is represented by formula (I):

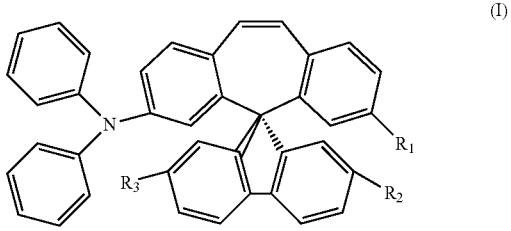

(I)

wherein $R_1$ is selected from a group consisting of formulas (II)-(VI):

(II)

(III)

(IV)

(V)

(VI)

wherein $R_2$ and $R_3$ are identical and selected from a group consisting of formula (VII) and formula (VIII):

$$—H \quad \text{(VII)}$$

$$-\underset{\underset{CH_3}{|}}{\overset{\overset{CH_3}{|}}{C}}-CH_3 \quad \text{(VIII)}$$

The optoelectronic materials possesses superior luminescent performance and thermal stability and is suitable to be a new type of ambipolar materials for OLED elements.

6 Claims, 3 Drawing Sheets

OPTOELECTRONIC MATERIALS FOR OLED AND OLED ELEMENTS USING THE SAME

FIELD OF THE INVENTION

The present invention relates to optoelectronic materials for OLED and OLED elements using the same, particularly to optoelectronic materials, which apply to OLED and possess superior luminescent performance and thermal stability, and OLED elements using the same.

BACKGROUND OF THE INVENTION

Recently, the increasing consumption of electronic products and the global trend to promote the illumination technology has encouraged LED (Light Emitting Diode) and OLED (Organic Light Emitting Diode) to develop rapidly and caused them to replace the conventional lighting devices gradually. The development of LED and OLED also influences the spin-off industries, such as the industries massively using display panels. Development of OLED seems to be relatively slower than LED. However, OLED has advantages of self-luminescence, low power consumption, flexibility, high contrast and slimness. Therefore, the related manufacturers have all been devoted to researching and developing OLED.

An ordinary OLED, such as that disclosed by a US patent No. 2009/0295278, comprises an anode, a cathode, and an organic light emitting unit. The organic light emitting unit includes a hole transport layer connecting with the anode, an electron transport layer connecting with the cathode, and an organic light emitting layer arranged between the hole transport layer and the electron transport layer. While a bias is applied to the anode and the cathode, holes and electrons are respectively injected into the hole transport layer and the electron transport layer. The bias drives the holes and electrons to move and recombine in the organic light emitting layer, whereby light is emitted.

In the current OLED technology, the light emitting layer, electron transport layer and hole transport layer made of ordinary optoelectronic materials, such as the well-known α-NPB, Alq$_3$, TPBI, etc., are insufficient to meet requirements of consumers. In order to solve the abovementioned problem, some manufacturers add extra layers to the existing light emitting layer, electron transport layer and hole transport layer to form a composite-structure OLED element and promote the overall performance thereof. Such a technology has a disadvantage: while an element malfunctions, the problem is hard to find out and solve quickly because of complicated structure. Further, the manufacturers have to spend considerable materials cost and fabrication cost in the composite-structure OLED, which makes the price hard to decrease and hinders OLED from replacing the conventional lighting elements.

SUMMARY OF THE INVENTION

The primary objective of the present invention is to overcome the poor performance of the conventional optoelectronic materials for OLED.

To achieve the abovementioned objective, the present invention proposes an optoelectronic material for OLED, which is represented by formula (I):

wherein $R_1$ is selected from a group consisting formulas (II)-(VI):

wherein $R_2$ and $R_3$ are identical and selected from a group consisting of formula (VII) and formula (VIII):

The present invention also proposes an OLED element, which comprises a substrate; a lower electrode formed on the substrate; a composite layer formed on the lower electrode; a hole transport layer formed on the composite layer; and an upper electrode formed on the hole transport layer, wherein the composite layer contains a optoelectronic material represented by formula (I).

In one embodiment of the present invention, the composite layer includes an electron transport layer formed on the lower electrode and a light emitting layer formed between the electron transport layer and the hole transport layer, wherein the emitting layer is made of an optoelectronic material represented by formula (I).

In one embodiment of the present invention, the composite layer includes an electron transport layer formed on the lower electrode and a light emitting layer formed between the electron transport layer and the hole transport layer, wherein the electron-transporting layer is made of a optoelectronic material represented by formula (I).

Via the abovementioned technical scheme, the present invention has the following advantages:

1. Dibenzosuberone is used as the core and integrated with Spiro-fluorene at $C_5$, Diphenylamine at $C_3$, and Cyano, 4-Cyanophenyl, or Benzimidazole at $C_7$, to form the optoelectronic material of the present invention. Diphenylamine at $C_3$ is an acceptor functional group. Cyano, 4-Cyanophenyl, or Benzimidazole at $C_7$ is a donor functional group. The abovementioned molecular design raises the glass transition temperature to 105-169° C. and raises the decomposition temperature to 385-492° C. Therefore, the optoelectronic materials of the present invention have fine thermal stability.
2. The optoelectronic materials of the present invention feature ambipolar properties with quasireversible reduction profiles. Either of the transfer rates of electrons and holes is within a range of $5 \times 10^{-6}$-$6 \times 10^{-6}$ cm$^2$/v·s. Even though the OLED devices of the optoelectronic materials of the present invention are operated at a current density of as high as 400 mA/cm$^2$ and a brightness of as high as 20000 nits, they can still maintain about 80% of operational performance. In contrast, the conventional optoelectronic materials (e.g. Alq$_3$ and bispirofluorene) can only keep about 60-70% of operational performance at a current density of as high as 400 mA/cm$^2$ and a brightness of as high as 20000 nits.
3. The OLEDs using the abovementioned photoelectronic materials of the present invention can achieve superior luminescent performance and has a maximum current efficiency $\eta_c$ of about 16 cd·A$^{-1}$, a maximum power efficiency $\eta_p$ of about 7 lm·W$^{-1}$, a maximum brightness of about 65,200 cd/m$^2$, and an external quantum efficiency $\eta_{ext}$ of about 5.3%.

DETAILED DESCRIPTION OF THE PREFERRED EMBODIMENTS

The technical contents of the present invention are described in detail in cooperation with the drawings shown below.

The present invention proposes a series of optoelectronic materials for OLED, which is represented by formula (I):

wherein $R_1$ is selected from a group consisting of formulas (II)-(VI):

(II)

(III)

(IV)

(V)

(VI)

wherein $R_2$ and $R_3$ are identical and selected from a group consisting of formula (VII) and formula (VIII):

—H (VII)

(VIII)

Figure 1:
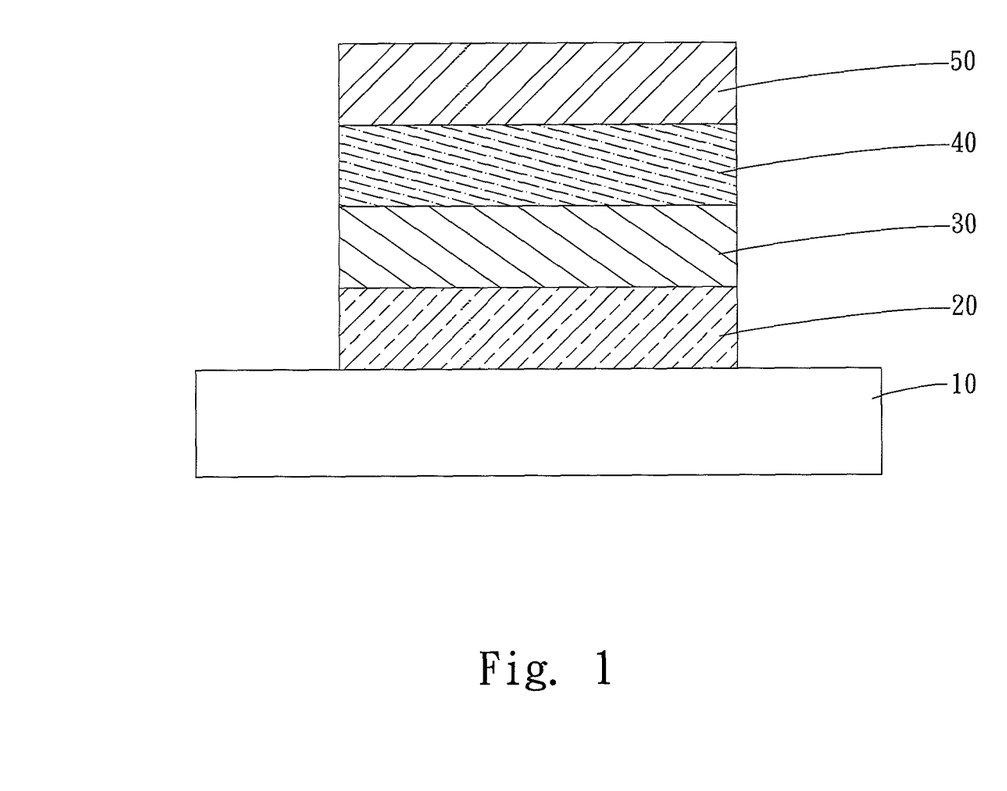
FIG. 1 schematically shows an OLED element according to a first embodiment of the present invention.

The present invention also proposes an OLED element. Refer to FIG. 1 a diagram schematically showing an OLED element according to a first embodiment of the present invention. The OLED element of the first embodiment comprises a substrate 10; a lower electrode 20 formed on the substrate 10; a composite layer 30 formed on the lower electrode 20; a hole transport layer 40 formed on the composite layer 30; and an upper electrode 50 formed on the hole transport layer 40.

In the first embodiment, the composite layer 30 adopts a single layer of the abovementioned optoelectronic materials represented by formula (I). Thereby, the OLED element of the first embodiment is a bilayer OLED element, as shown in FIG. 1. In the first embodiment, the substrate 10 is made of aluminum; the lower electrode 20 is made of LiF (Lithium Fluoride) and has a thickness of 1 nm; the composite layer 30 is made of the abovementioned optoelectronic materials represented by formula (I) and has a thickness of 40 nm; the hole transport layer 40 is made of α-NPB and has a thickness of 40 nm; the upper electrode 50 is made of ITO (Indium Tin Oxide).

Figure 2:
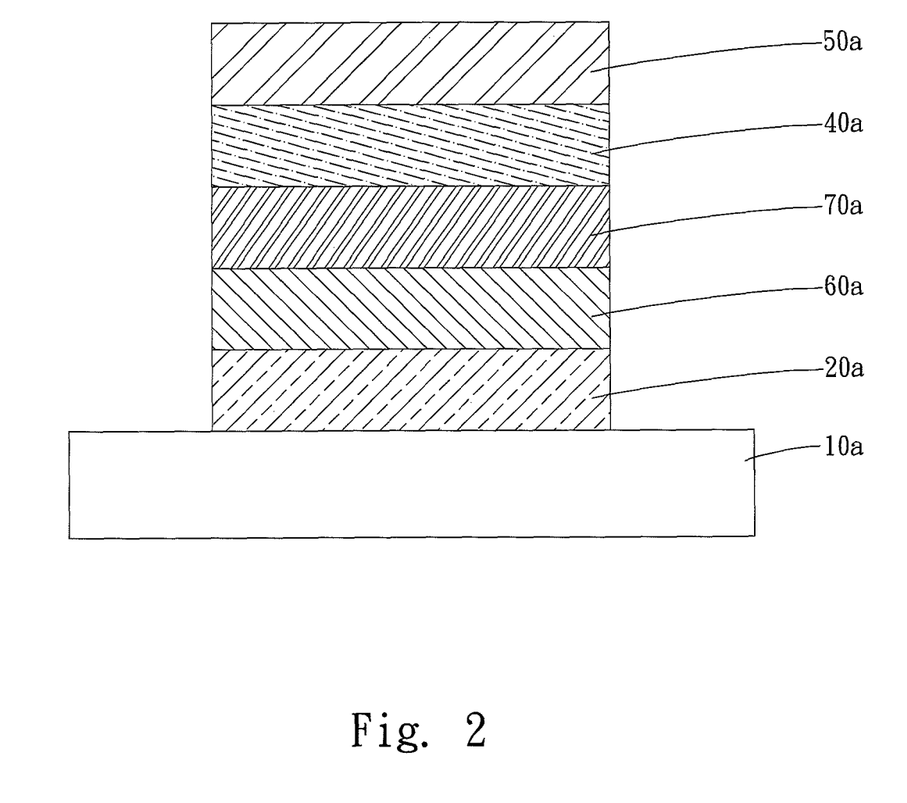
FIG. 2 schematically shows an OLED element according to a second embodiment of the present invention.

Refer to FIG. 2 a diagram schematically showing an OLED element according to a second embodiment of the present invention. In the second embodiment, the composite layer 30 includes an electron transport layer 60a and a light emitting layer 70a. In other words, the OLED element of the second embodiment comprises a substrate 10a; a lower electrode 20a formed on the substrate 10a; an electron transport layer 60a formed on the lower electrode 20a; a light emitting layer 70a formed on the electron transport layer 60a; a hole transport layer 40a formed on the light emitting layer 70a; and an upper electrode 50a formed on the hole transport layer 40a. In the second embodiment, the light emitting layer 70a adopts a single layer of the abovementioned optoelectronic materials. Thereby, the OLED element of the second embodiment is a trilayer OLED element. In the second embodiment, the substrate 10a is made of aluminum; the lower electrode 20a is made of LiF (Lithium Fluoride) and has a thickness of 1 nm; the electron transport layer 60a is made of TPBI and has a thickness of 40 nm; the light emitting layer 70a is made of the abovementioned optoelectronic materials represented by formula (I) and has a thickness of 40 nm; the hole transport layer 40a is made of NPB and has a thickness of 40 nm; the upper electrode 50a is made of ITO (Indium Tin Oxide).

Figure 3:
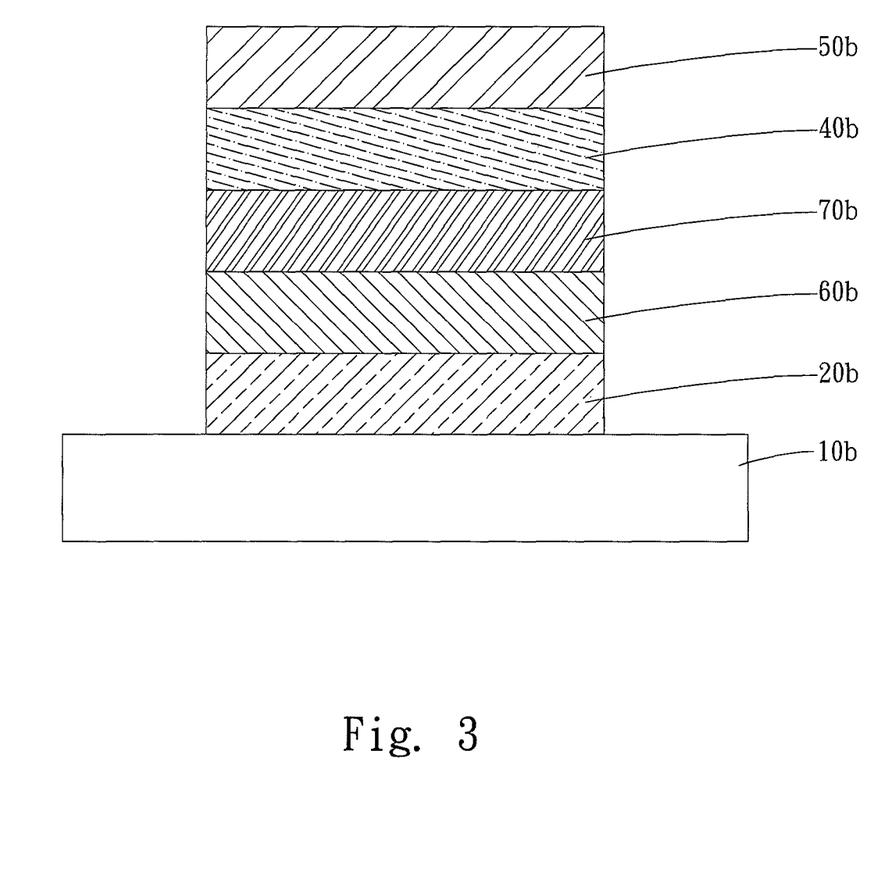
FIG. 3 schematically shows an OLED element according to a third embodiment of the present invention.

Refer to FIG. 3 a diagram schematically showing an OLED element according to a third embodiment of the present invention. In the third embodiment, the composite layer 30 includes an electron transport layer 60b and a light emitting layer 70b. In other words, the OLED element of the third embodiment comprises a substrate 10b; a lower electrode 20b formed on the substrate 10b; an electron transport layer 60b formed on the lower electrode 20b; a yellow light emitting layer 70b formed on the electron transport layer 60b; a hole transport layer 40b formed on the light emitting layer 70b; and an upper electrode 50b formed on the hole transport layer 40b. In the third embodiment, the electron transport layer 60b adopts a composite layer of BCP and the abovementioned optoelectronic materials. Thereby, the OLED element of the third embodiment is a trilayer OLED element.

Below, experiments are used to further demonstrate the optoelectronic materials for OLED and the OLED elements using the same of the present invention. However, these experiments are only to exemplify the present invention but not to limit the scope of the present invention.

Experiment I

Use potassium hexacyanoferrate(II) ($K_4[Fe(CN)_6]$) and palladium (Pd) metal to catalyze the reaction of Diphenylamine and a compound represented by formula (1) in a Hartwig method to obtain a compound represented by formula (2), as shown by the following reaction formula:

Next, use a Rosemund-VonBarann method to fabricate the compound represented by formula (2) into a compound represented by formula (3), as shown by the following reaction formula:

Thus is obtained the product of Experiment I the compound represented by formula (3).

Experiment II

Use palladium metal to catalyze a Suzuki coupling reaction of 4-cyanophenylbronic acid and the compound represented by formula (2) to obtain a compound represented by formula (4), as shown by the following reaction formula:

Thus is obtained the product of Experiment II the compound represented by formula (4).

Experiment III

Add n-butyllithium to the compound obtained in Experiment I and represented by formula (2) to undergo a formylation reaction at a temperature of −78° C. Next, add p-toluenesulfonic acid (p-TSA) dissolved in Tetrahydrofuran (THF) at the same temperature to quench the reaction. Via the purification processes of evaporation, extraction and column chromatography sequence is obtained a compound represented by formula (7), as shown by the following reaction formula:

Next, dissolve the compound represented by formula (7) and N-phenyl-o-phenylenediamine in benzene, and add p-TSA to the benzene solution to undergo a reaction under refluxing temperature for 36 hours, as shown by the following reaction formula:

Then, quench the reaction. Via the purification processes of evaporation, extraction and column chromatography is obtained a compound represented by formula (8), which is exactly the product of Experiment III.

Experiment IV

Dissolve 2-bromo-4,4-tert-butylbiphenyl and n-butyllithium in THF to generate a lithiated reagent at a temperature of −78° C. Next, dropwise addition the lithium reagent into a mixture containing 3,7-dibromo-dibenzosuberenone and THF at a temperature of −78° C. generates a tertiary alcohol compound. Next, intramolecular Friedel-Crafts reaction of the tertiary alcohol compound in an acidic environment can provide a compound represented by formula (9), as shown by the following reaction formula:

Next, Hartwig reaction of Diphenylamine and the compound represented by formula (9) can provide an intermediate product represented by formula (10), as shown by the following reaction formula:

(9)

(11)

(10)

Next, condensation reaction of N-phenyl-o-phenylenediamine and the compound represented by formula (11) in an acidic state can provide a compound represented by formula (12), as shown by the following reaction formula:

(11)

(12)

Next, use palladium metal to catalyze a Suzuki coupling reaction of 4-formylphenylbronic acid and the intermediate product represented by formula (10) to obtain a compound represented by formula (11), as shown by the following reaction formula:

(10)

Thus is obtained the product of Experiment IV—the compound represented by formula (12).

Experiment V

Add n-butyllithium to the compound obtained in Experiment I and represented by formula (2) to undertake a reaction at a temperature of −78° C. for 2 hours to generate a lithiated reagent. Next, add diphenylphosphinous chloride to the lithiated reagent to undergo a reaction at an ambient temperature for 12 hours, as shown by the following reaction formula. Next, use water to quench the abovementioned reaction. Via the purification processes of evaporation, extraction and column chromatography is obtained a compound represented by formula (13).

(2)

(13)

Next, dissolve the compound represented by formula (13) in methylene chloride. Next, the aqueous solution of 30% hydrogen peroxide was added dropwise into the methylene chloride solution at an ambient temperature to undergo a reaction for 2 hours at the same temperature, as shown by the following reaction formula:

(13)

(14)

Via the purification processes of evaporation, extraction and column chromatography is obtained a compound represented by formula (14), which is exactly the product of Experiment V.

In order to fully understand the thermal properties, optical properties and chemical properties of the optoelectronic materials of the present invention, DSC (Differential Scanning calorimetry) and TGA (Thermogravimetric Analysis) are used to measure $T_g$ (Glass Transition Temperature) and $T_d$ (Decomposition Temperature); Ultraviolet-visible Spectroscopy is used to obtain the lowest energy peaks of the absorption spectrum; Photoluminescence Spectroscopy are used to obtain the peaks of the emission spectrum; CV (Cyclic Voltammetry) is used to measure the potentials of oxidation and reduction.

TABLE 1

| Serial Number | $T_g$ (°C.) | $T_d$ (°C.) | $\lambda_{max}$ ($\epsilon_{max} \times 10^{-3}$)(nm) | PL$\lambda_{max}$ ($\Phi_f\%$)$^a$(nm) |
|---|---|---|---|---|
| Experiment I | 105 | 389 | 420(25.8) | 519(87) |
| Experiment II | 130 | 385 | 410(15.8) | 523(62) |
| Experiment III | 140 | 435 | 408(25.2) | 505(62) |
| Experiment IV | 169 | 492 | 402(29.7) | 510(94) |
| Experiment V | 121 | 492 | 406(21.4) | 501(79) |

TABLE 2

| Serial Number | $E^{ox}_{1/2}/E^{red}_{1/2}, V^b$ | $E_g, eV^b$ |
|---|---|---|
| Experiment I | +0.48/−2.27 | 2.59 |
| Experiment II | +0.45/−2.33, −2.67 | 2.62 |
| Experiment III | +0.45/−2.36 | 2.65 |
| Experiment IV | +0.41/−2.44, −2.67 | 2.68 |
| Experiment V | +0.40/−2.34 | 2.74 |

From the tables shown above, it is learned: the glass transition temperatures ($T_g$) of the optoelectronic materials of Experiments I-V all exceed 105° C., and the decomposition temperatures ($T_d$) of the optoelectronic materials of Experiments I-V all exceed 385° C. The optoelectronic material of Experiment V has the best thermal properties, wherein the glass transition temperature ($T_g$) thereof reaches as high as 169° C., and the decomposition temperature ($T_d$) thereof reaches as high as 492° C. Therefore, the optoelectronic materials of the present invention indeed possess superior thermal stability. Further, the optoelectronic materials of the present invention are hard to vitrify or decompose under high applied voltage or high current density and thus less likely to degrade in efficiency by high applied voltage or high current density. Besides, the optoelectronic materials of the present invention have superior quasireversible oxidation and reduction potentials, which prove the ambipolar property of the optoelectronic materials of the present invention.

In order to analyze the OLED luminescent performances of the optoelectronic materials of Experiments I-V, the optoelectronic properties of the OLED elements using the optoelectronic materials of Experiments I-V are measured, including the electroluminescence spectrum ($E_m$), the turn-on voltage ($V_{on}$), the operating voltage (V), the external quantum efficiency ($\eta_{ext}$), the current efficiency ($\eta_c$), the power efficiency ($\eta_p$), the maximum luminescence ($L_{max}$), the operating luminescence ($L_{20}$), wherein the values of the turn-on voltage ($V_{on}$), the external quantum efficiency ($\eta_{ext}$), the current efficiency ($\eta_c$), the power efficiency ($\eta_p$), and the operating luminescence ($L_{20}$) are all measured at a current density of 20 mA/cm².

Table.3 shows the device configuration designs of the OLED elements. Table.4 shows the optoelectronic properties of the OLED elements. The value in parenthesis of the electroluminescence spectrum ($E_m$) is the full width at half maximum (FWHM), and the unit thereof is nm. The unit of the turn-on voltage ($V_{on}$) and the operating voltage (V) is eV. The unit of the external quantum efficiency ($\eta_{ext}$) is %. The unit of the current efficiency ($\eta_c$) is cd/A. The unit of the power efficiency ($\eta_p$) is lm/W. The unit of the maximum luminescence ($L_{max}$) and the operating luminescence ($L_{20}$) is cd/m².

TABLE 3

| Serial Number | Substrate | Lower electrode | Electron transport layer | Light emitting layer | Hole transport layer | Upper electrode |
|---|---|---|---|---|---|---|
| Element 1 | Al | LiF | TPBI | Experiment I | NPB | ITO |
| Element 2 | Al | LiF |  | Experiment 1 | NPB | ITO |
| Element 3 | Al | LiF | TPBI | Experiment II | NPB | ITO |
| Element 4 | Al | LiF |  | Experiment II | NPB | ITO |
| Element 5 | Al | LiF | TPBI | Experiment III | NPB | ITO |
| Element 6 | Al | LiF |  | Experiment III | NPB | ITO |
| Element 7 | Al | LiF | TPBI | Experiment IV | NPB | ITO |
| Element 8 | Al | LiF |  | Experiment IV | NPB | ITO |
| Element 9 | Al | LiF | TPBI | Experiment V | NPB | ITO |
| Element 10 | Al | LiF |  | Experiment V | NPB | ITO |
| Comparison 1 | Al | LiF |  | Alq$_3$ | NPB | ITO |

TABLE 4

| Serial Number | $E_m$ ($\lambda_{max}$) | $V_{on}$ (V) | $\eta_{ext}$ | $\eta_c/\eta_p$ | $L_{max}$ ($L_{20}$) |
|---|---|---|---|---|---|
| Element 1 | 522 (85) | 2.7 (6.0) | 4.0 | 13.4/7.0 | 38901 (2551) |
| Element 2 | 514 (83) | 3.8 (5.7) | 1.6 | 5.3/3.1 | 21879 (1086) |
| Element 3 | 524 (90) | 3.0 (8.0) | 4.0 | 13.8/5.4 | 65182 (2756) |
| Element 4 | 516 (78) | 2.6 (6.0) | 3.1 | 10.5/5.4 | 55120 (2094) |
| Element 5 | 506 (89) | 2.4 (7.6) | 5.3 | 15.8/6.6 | 51030 (3069) |
| Element 6 | 497 (79) | 4.1 (7.0) | 1.7 | 4.6/2.1 | 20272 (928) |
| Element 7 | 500 (83) | 3.8 (6.3) | 4.0 | 11.5/6.1 | 51659 (2202) |
| Element 8 | 490 (87) | 3.8 (6.3) | 4.2 | 11.4/6.0 | 21971 (2179) |
| Element 9 | 500 (80) | 2.5 (4.4) | 6.65 | 6.9/5.0 | 30650 (1375) |
| Element 10 | 500 (81) | 2.5 (4.8) | 3.47 | 3.6/2.4 | 23600 (721) |
| Comparison 1 | 516 (104) | 3.9 (5.6) | 1.1 | 3.3/1.8 | 28911 (638) |

From the tables shown above, it is learned: Element 4 using the molecule of Experiment II as the composite layer outperforms Comparison 1 (the bilayer OLED element using Alq$_3$ as the light emitting layer and the electron transport layer) in the external quantum efficiency ($\eta_{ext}$), the current efficiency ($\eta_c$), the power efficiency ($\eta_p$), and the operating luminosity ($L_{20}$) under the same operating voltage; Elements 8 and 10 using the molecules of Experiments IV and V, respectively, as the composite layer also far outperforms Comparison 1 in the external quantum efficiency ($\eta_{ext}$), the current efficiency ($\eta_c$), the power efficiency ($\eta_p$), and the operating luminosity ($L_{20}$). Therefore, the photoelectronic materials of the present invention possess superior luminescent properties.

Table.5 shows the external quantum efficiency ($\eta_{ext}$), the maximum power efficiency (PE) and the maximum current efficiency (LE) of Element 1, Element 3, Element 5, Element 7, and Element 9, which are measured under an operational luminescence of about 2000 cd/m² and a high luminescence of about 20000 cd/m². Table.6 shows the external quantum efficiency ($\eta_{ext}$), the maximum power efficiency (PE) and the maximum current efficiency (LE) of Element 1, Element 3, Element 5, Element 7, and Element 9, which are measured under an operational current density of about 20 mA/cm² and a high current density of about 400 mA/cm².

TABLE 5

| Serial Number | Luminosity (cd/cm²) | $\eta_{ext}$ | LE (cd/A) | PE (lm/w) |
|---|---|---|---|---|
| Element 1 | 2,000 nits | 4.3% | 13.6 | 8.3 |
|  | 20,000 nits | 3.0% | 9.2 | 3.8 |
| Element 3 | 2,000 nits | 4.2% | 14.2 | 5.7 |
|  | 20,000 nits | 3.4% | 11.6 | 3.6 |
| Element 5 | 2,000 nits | 5.3% | 16.2 | 6.9 |
|  | 20,000 nits | 3.9% | 11.7 | 3.9 |
| Element 7 | 2,000 nits | 3.8% | 10.9 | 5.8 |
|  | 20,000 nits | 3.4% | 9.5 | 3.7 |
| Element 9 | 2,000 nits | 6.3% | 6.8 | 4.5 |
|  | 20,000 nits | 5.0% | 5.0 | 2.0 |

TABLE 6

| Serial Number | Current density (mA/cm²) | $\eta_{ext}$ | LE (cd/A) | PE (lm/w) |
|---|---|---|---|---|
| Element 1 | 20 | 3.8% | 12.7 | 6.6 |
|  | 400 | 2.4% | 7.8 | 2.5 |
| Element 3 | 20 | 4.1% | 13.8 | 5.4 |
|  | 400 | 3.2% | 10.6 | 3.1 |
| Element 5 | 20 | 5.1% | 15.5 | 6.4 |
|  | 400 | 3.3% | 9.7 | 2.9 |
| Element 7 | 20 | 3.9% | 11.0 | 5.7 |
|  | 400 | 3.2% | 9.0 | 2.9 |
| Element 9 | 20 | 6.7% | 7.0 | 5.0 |
|  | 400 | 4.9% | 5.0 | 2.0 |

From the tables shown above, it is learned: the elements using the optoelectronic materials of the present invention can still maintain 80% of the operating capacity at a high current density or a high luminescence (about 20000 cd/m²). While the optoelectronic materials of the present invention are used as the only light emitting layer or as light emitting layer and the electron transport layer simultaneously, the overall performance of the element are also very prominent. Especially, the element using the optoelectronic materials of the present invention as the light emitting layer(s) and the electron transport layer outperforms the Alq$_3$-based bilayer OLED element by 1-3 times.

In the tests for verifying the performance of the optoelectronic materials in the cases that they are used only as the electron-transporting layer of OLED elements, the materials of Experiment I and Experiment II are used as exemplifications of the materials of the present invention. Table.7 shows the device configuration designs of the OLED elements. Table.8 shows the optoelectronic properties of the OLED elements. The value in parenthesis of the electroluminescent spectrum ($E_m$) is the full width at half maximum (FWHM), and the unit thereof is nm. The unit of the turn-on voltage ($V_{on}$) and the operating voltage (V) is eV. The unit of the external quantum efficiency ($\eta_{ext}$) is %. The unit of the current efficiency ($\eta_c$) is cd/A. The unit of the power efficiency ($\eta_p$) is lm/W. The unit of the maximum luminescence ($L_{max}$) and the operating luminosity ($L_{20}$) is Cd/m².

TABLE 7

| Serial Number | Substrate | Lower electrode | Electron transport layer | Light emitting layer | Hole transport layer | Upper electrode |
|---|---|---|---|---|---|---|
| Element 11 | Al | LiF | BCP/Expt. I | Yellow emitter | NPB | ITO |
| Element 12 | Al | LiF | BCP/Expt. II | Yellow emitter | NPB | ITO |
| Comparison 2 | Al | LiF | BCP/Alq$_3$ | Yellow emitter | NPB | ITO |

Yellow emitter

TABLE 8

| Serial Number | $E_m$ ($\lambda_{max}$) | $V_{on}$ (V) | $\eta_{ext}$ | $\eta_c/\eta_p$ | $L_{max}$ ($L_{20}$) |
|---|---|---|---|---|---|
| Element 11 | 586 (95) | 3.4 (6.2) | 5.0 | 12.3/6.3 | 32400(2433) |
| Element 12 | 586 (95) | 3.6 (7.0) | 4.2 | 10.6/4.8 | 22830(2119) |
| Comparison 2 | 581 (88) | 3.4 (6.3) | 2.7 | 7.1/3.6 | 16660(1391) |

From the tables shown above, it is learned: the optoelectronic materials of the present invention still have superior luminescent performance while they are used only as the electron transporting layer of OLED elements.

In conclusion, Dibenzosuberone is used as the core and integrated with Spiro-fluorene at $C_5$, Diphenylamine at $C_3$, and Cyano, 4-Cyanophenyl, or Benzimidazole at $C_7$, to form the optoelectronic materials of the present invention. Diphenylamine at $C_3$ is an acceptor functional group. Cyano, 4-Cyanophenyl, or Benzimidazole at $C_7$ is a donor functional group. The abovementioned molecular design raises the glass transition temperature to 105-169° C. and raises the decomposition temperature to 385-492° C. Therefore, the optoelectronic materials of the present invention have fine thermal stability. No matter whether the optoelectronic materials of the present invention are used as a composite layer (i.e. the optoelectronic materials function as light emitting layer or as a light emitting layer and an electron transport layer simultaneously) or independently used as a an electron transport layer, it can always exhibit superior luminescent properties than those of the corresponding $Alq_3$ based devices.

What is claimed is:

1. An optoelectronic materials for an organic light emitting diode, which is represented by formula (I):

(I)

wherein $R_1$ is selected from a group consisting of the formulas (II)-(VI):

(II)

(III)

(IV)

(V)

(VI)

wherein $R_2$ and $R_3$ are identical and selected from a group consisting of the formula (VII) and formula (VIII):

(VII)

(VIII)

2. The optoelectronic materials for an organic light emitting diode according to claim 1, which have a glass transition temperature of 105-169° C.

3. The optoelectronic materials for an organic light emitting diode according to claim 1, which have a decomposition temperature of 385-492° C.

4. An organic light emitting diode element comprising
a substrate;
a lower electrode formed on the substrate;
a composite layer formed on the lower electrode;
a hole transport layer formed on the composite layer; and
an upper electrode formed on the hole transport layer,
wherein the composite layer contains the optotoelectronic material for an organic light emitting diode according to claim 1.

5. The organic light emitting diode element according to claim 4, wherein the composite layer includes an electron transport layer formed on the lower electrode and a light emitting layer formed between the electron transport layer and the hole transport layer, and wherein the light emitting layer contains the optoelectronic materials represented by formula (I).

6. The organic light emitting diode element according to claim 4, wherein the composite layer includes BCP and an electron transport layer formed on the lower electrode and a yellow light emitting layer formed between the electron transport layer and the hole transport layer, and wherein the electron-transport layer contains the optoelectronic material represented by formula (I).

* * * * *